US00PP33085P2

(12) United States Plant Patent
van Langen

(10) Patent No.: US PP33,085 P2
(45) Date of Patent: May 18, 2021

(54) ***SENECIO* PLANT NAMED 'AMICU1907'**

(50) Latin Name: ***Senecio* hybrid**
Varietal Denomination: AMICU1907

(71) Applicant: NovoAmi B. V., Heerhugowaard (NL)

(72) Inventor: Gerard van Langen, Heerhugowaard (NL)

(73) Assignee: NovoAmi B. V., Heerhugowaard (NL)

( * ) Notice: Subject to any disclaimer, the term of this patent is extended or adjusted under 35 U.S.C. 154(b) by 0 days.

(21) Appl. No.: 16/895,165

(22) Filed: Jun. 8, 2020

(51) Int. Cl.
*A01H 5/12* (2018.01)
*A01H 6/14* (2018.01)

(52) U.S. Cl.
USPC ..... Plt./480

(58) Field of Classification Search
USPC ..... Plt./480
See application file for complete search history.

*Primary Examiner* — Susan McCormick Ewoldt
(74) *Attorney, Agent, or Firm* — Samuel R. McCoy, Jr.

(57) ABSTRACT

A new and distinct *Senecio* plant named 'AMICU1907' which is characterized by a compact and upright growth habit, a glaucous blue-green stem, glaucous blue-green foliage, narrowly oblanceolate and falcate foliage, semi-terete to terete foliage with an obvious longitudinal channel running the length of the leaf, and the stability of these characteristics from generation to generation.

2 Drawing Sheets

Latin name of the genus and species: The Latin name of the genus and species of the novel variety disclosed herein is *Senecio* hybrid.

Variety denomination: The inventive variety of *Senecio* disclosed herein has been given the variety denomination 'AMICU1907'.

BACKGROUND OF THE INVENTION

Parentage: 'AMICU1907' is a seedling selection resulting from the controlled pollination of an unnamed *Senecio kleiniiformis* plant (not patented), the seed parent, with an unnamed *Curio ficoides* plant (not patented), the pollen parent. The crossing was made by the inventor in the spring of 2018 at a commercial greenhouse in Heerhugowaard, the Netherlands. In the autumn of 2018, one seedling resulting from the crossing was observed to exhibit unique growth and foliage characteristics and was isolated for further evaluation in order to confirm the distinctness and stability of the characteristics first observed. Upon confirmation of distinctness and stability, 'AMICU1907' was selected for commercialization.

Asexual Reproduction: Asexual reproduction of the new cultivar 'AMICU1907', by way of rooting leaf cuttings, was first initiated in the winter of 2018 at the inventor's commercial greenhouse in Heerhugowaard, the Netherlands. Through four subsequent generations, the unique features of this cultivar have proven to be stable and true to type.

SUMMARY OF THE INVENTION

The cultivar 'AMICU1907' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMICU1907'. These characteristics in combination distinguish 'AMICU1907' as a new and distinct *Senecio* cultivar:

1. 'AMICU1907' exhibits a compact growth habit with a single near-vertical stem bearing foliage that is held upright and outward; and
2. 'AMICU1907' exhibits a glaucous yellow-green stem, generally appearing as a blue-green coloration due to the thick layer of blue-green epicuticular wax; and
3. 'AMICU1907' exhibits glaucous yellow-green to green foliage, generally appearing as a blue-green coloration due to the thick layer of blue-green epicuticular wax; and
4. 'AMICU1907' exhibits narrowly oblanceolate, falcate and terete foliage with a longitudinal channel running the length of the leaf.

BOTANICAL DESCRIPTION OF THE PLANT

Figure 1:
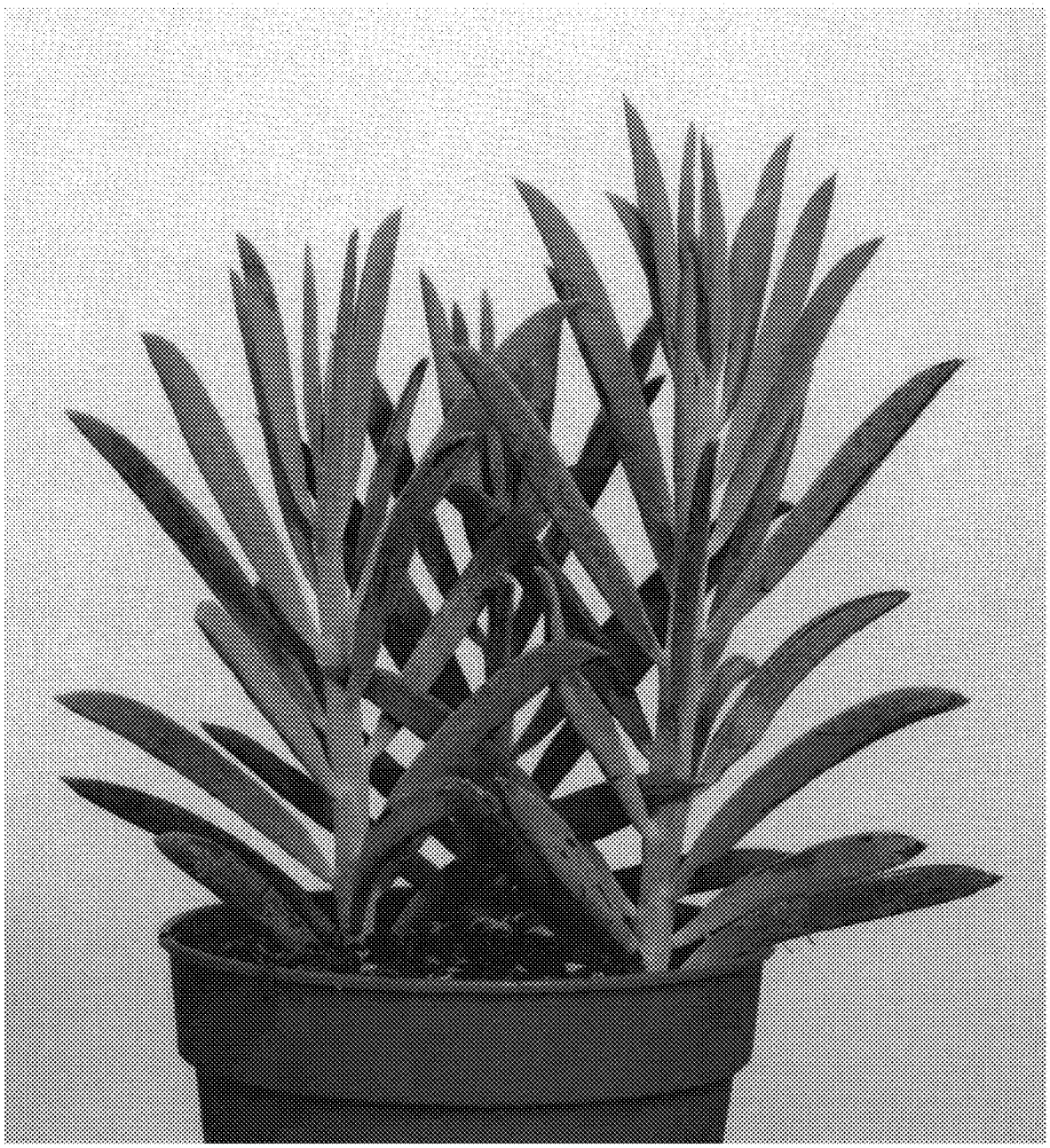
FIG. 1 illustrates, as nearly true as it is reasonably possible to make the same in color photographs of this type, three exemplary plants of 'AMICU1907' grown in a commercial greenhouse in Heerhugowaard, the Netherlands. The plants are approximately 12 months old, shown planted in an 11 cm container.
Figure 2:
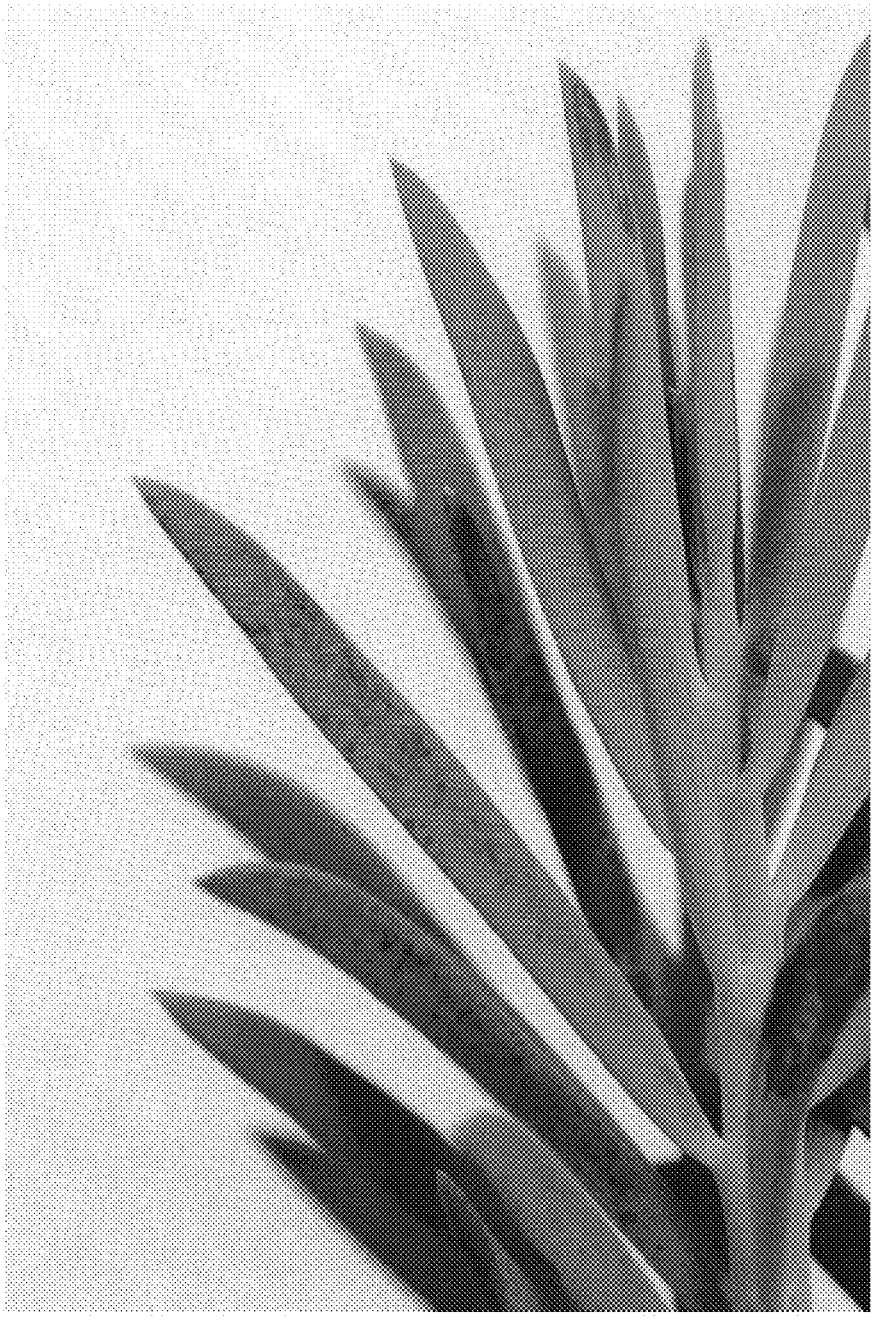
FIG. 2 illustrates, as nearly true as it is reasonably possible to make the same in color photographs of this type, the typical foliage of 'AMICU1907'.

The following observations and measurements made in January of 2020 describe averages from a sample set of three specimens of 12 months old 'AMICU1907' plants grown in 11 cm nursery containers at commercial greenhouse in Heerhugowaard, the Netherlands. Plants were produced using conventional greenhouse production protocols for *Senecio* plants which consisted of minimal irrigation and fertilizer applications, and chemical pest and disease control measures against mealy bug and Botrytis as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMICU1907' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMICU1907' and comparisons with the parent plants and closest known comparator are provided below.

Plant description:

*Growth habit*.—Upright succulent perennial with foliage borne on a single unbranched stem.

*Plant profile*.—Ovate.

*Height from soil level to top of foliar plane*.—15.0 cm.

*Plant spread*.—Average of 13.2 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 25 weeks to produce a marketable plant in an 7 cm container.

*Disease and pest resistance or susceptibility*.—Plants have not been observed to be any more or less susceptible or resistant to pathogens and pests common to *Senecio* spp.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves borne on a single unbranched stem; no lateral branching.

*Quantity of main stems*.—1.

*Main stem dimensions*.—10.2 cm long and 0.7 cm in diameter.

*Internode length*.—0.6 cm.

*Aspect*.—Rounded.

*Attitude*.—Nearly vertical.

*Strength*.—Moderately strong.

*Texture and luster*.—Glabrous, glaucous, matte.

*Fragrance*.—When crushed, stem exhibits a somewhat spicy fragrance typical of the species.

*Color, when developing*.—Yellow-green, nearest to RHS 144A; stem covered with a thick waxy layer colored blue-green, nearest to RHS 122D.

*Color of mature stem*.—Yellow-green, nearest to RHS 144A; stem covered with a thick waxy layer colored blue-green, nearest to RHS 122D.

*Color at internodes*.—Yellow-green, nearest to RHS 144A; stem covered with a thick waxy layer colored blue-green, nearest to RHS 122D.

Foliage:

*Arrangement*.—Alternate.

*Division*.—Simple.

*Attachment*.—Sessile.

*Quantity*.—Approximately 23 leaves per stem.

*Shape*.—Narrow oblanceolate; distally falcate.

*Dimensions*.—7.9 cm long, 0.4 cm wide, and 0.8 cm thick, on average.

*Aspect*.—Semi-terete to terete, typically with an obvious longitudinal channel.

*Attitude*.—At an average angle of 45 degrees to the stem.

*Apex*.—Narrowly acute.

*Base*.—Cuneate.

*Margin*.—Entire; not undulated.

*Pubescence, texture and luster of the adaxial surface*.—Glabrous, smooth, and matte; strongly glaucous.

*Pubescence, texture and luster of the abaxial surface*.—Glabrous, smooth, and matte; strongly glaucous.

*Fragrance*.—When crushed, foliage exhibits a somewhat spicy fragrance typical of the species.

*Color*.—Juvenile foliage, adaxial surface — Yellow-green, nearest to RHS 147A; the epicuticular wax covering the leaf surface is nearest to in between blue-green and greyed-green, RHS 122D and 188C. Juvenile foliage, abaxial surface — Yellow-green, nearest to RHS 147A; the epicuticular wax covering the leaf surface is nearest to in between blue-green and greyed-green, RHS 122D and 188C. Mature foliage, adaxial surface — Nearest to in between yellow-green and green, RHS 147A and NN137A; the epicuticular wax covering the leaf surface is nearest to in between blue-green and greyed-green, RHS 122D and 188C. Mature foliage, abaxial surface — Nearest to in between yellow-green and green, RHS 147A and NN137A; the epicuticular wax covering the leaf surface is nearest to in between blue-green and greyed-green, RHS 122D and 188C.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'AMICU1907' differ from the seed parent, an unnamed and unpatented *Senecio kleiniiformis* plant, in the following characteristics described in Table 1 below.

TABLE 1

| Characteristic | 'AMICU1907' | The seed parent. |
|---|---|---|
| Foliage aspect and shape. | Semi-terete to terete and narrow oblanceolate. | Proximally terete, progressing to semi-terete and ultimately opening up, distally, to a deltoid shape. |
| Foliage strength. | Stronger than the parent. | Weaker than 'AMICU1907'. |

Plants of the new cultivar 'AMICU1907' differ from the pollen parent, unnamed and unpatented *Curio ficoides* plant, in the following characteristics described in Table 2 below.

TABLE 2

| Characteristic | 'AMICU1907' | The pollen parent |
|---|---|---|
| Stem diameter. | Thinner than the parent. | Thicker than 'AMICU1907'. |
| Foliage width. | Narrower than the parent. | Broader than 'AMICU1907'. |
| Foliage shape. | Narrow oblanceolate and distally falcate. | Oblanceolate; not falcate. |
| Foliage aspect. | Semi-terete to terete; typically with an obvious longitudinal channel. | Terete; longitudinal channel is less prominent. |
| General coloration of the foliage. | In between greyed-green and blue-green, yet generally presenting closer to green by comparison to the pollen parent. | In between greyed-green and blue-green, generally presenting as closer to a mixture of light gray and blue-green by comparison to 'AMICU1907'. |

COMPARISONS WITH THE CLOSEST KNOWN COMPARATOR

Plants of the new cultivar 'AMICU1907' differ from the closest known commercial comparator, the common form of the species *Senecio ficoides* 'Mount Everest' (U.S. Plant Pat. No. 22,188), in the following characteristics described in Table 3 below.

TABLE 3

| Characteristic | 'AMICU1907' | 'Mount Everest' |
|---|---|---|
| Growth habit. | More compact than 'Mount Everest'. | Less compact than 'AMICU1907'. |
| Plant height. | Shorter than 'Mount Everest'. | Taller than 'AMICU1907'. |
| Foliage aspect. | Semi-terete to terete; typically with an obvious longitudinal channel. | Terete; longitudinal channel is less prominent. |
| Foliage shape. | Narrow oblanceolate and distally falcate. | Oblanceolate; not falcate. |

That which is claimed is:

1. A new and distinct variety of *Senecio* plant named 'AMICU1907', substantially as described and illustrated herein.

* * * * *